United States Patent [19]

Spelsberg

[11] 4,307,846
[45] Dec. 29, 1981

[54] CONTINUOUS FLOW TISSUE HOMOGENIZER

[76] Inventor: Thomas C. Spelsberg, 1828 Walden La. South West, Rochester, Minn. 55901

[21] Appl. No.: 82,671

[22] Filed: Oct. 9, 1979

[51] Int. Cl.³ ............................................ B02C 19/00
[52] U.S. Cl. ........................................ 241/246; 241/2; 241/169.1; 241/258; 241/259
[58] Field of Search ................... 241/2, 169.1, 169.2, 241/246, 248, 257 R, 258, 259, 245

[56] References Cited

U.S. PATENT DOCUMENTS

| | | | |
|---|---|---|---|
| 581,836 | 5/1897 | Taylor | 241/246 |
| 1,021,950 | 4/1912 | Shepard. | |
| 2,749,053 | 6/1956 | Rieth | 241/162 |
| 2,886,253 | 5/1959 | Skibicki et al.. | |
| 2,963,232 | 12/1960 | Smith | 241/259 |
| 3,236,743 | 2/1966 | Pierson. | |
| 3,298,411 | 1/1967 | Rosett. | |
| 3,587,982 | 6/1971 | Campbell | 241/2 X |
| 3,724,765 | 4/1973 | Rohrbaugh et al. | 241/169.1 UX |
| 3,750,964 | 8/1973 | Cohen et al. | 241/29 |
| 3,912,179 | 10/1975 | Hartig, Jr. et al. | 241/248 X |

FOREIGN PATENT DOCUMENTS 682266  8/1979  U.S.S.R. ............................ 241/2

*Primary Examiner*—Mark Rosenbaum
*Attorney, Agent, or Firm*—Merchant, Gould, Smith, Edell, Welter & Schmidt

[57] ABSTRACT

A continuous flow tissue homogenizer is disclosed and includes a generally tubular container (12) with an inner surface (60) defining a tissue homogenization chamber (19). One end of the container has an inlet (46) for the introduction of non-homogenized tissue in solution and the other end of the container has an outlet (36) for the discharge of homogenate. A pestle member (38) is disposed within the homogenization chamber and mounted to a shaft (40) for rotatably driving the pestle member. The pestle member has an outer surface (62) that is spaced apart from the inner surface of the container to provide a tissue disruption zone (64) therebetween. The pestle member divides the homogenization chamber into first portion (54) and second portion (56). A plurality of grooves (68) are circumferentially spaced about the outer surface of the pestle member and open into the first chamber portion to channel the tissue solution into the tissue disruption zone of the apparatus.

10 Claims, 9 Drawing Figures

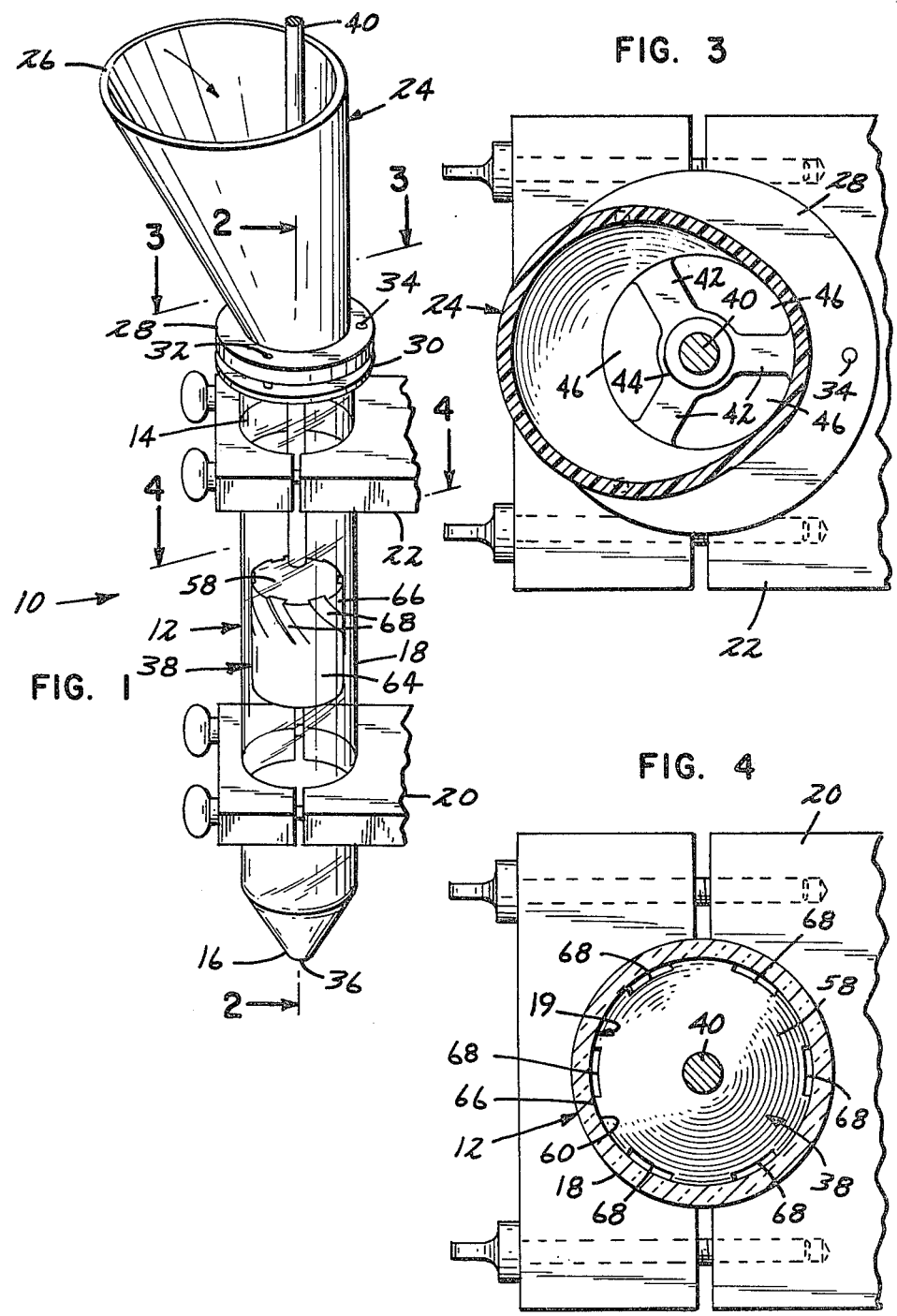

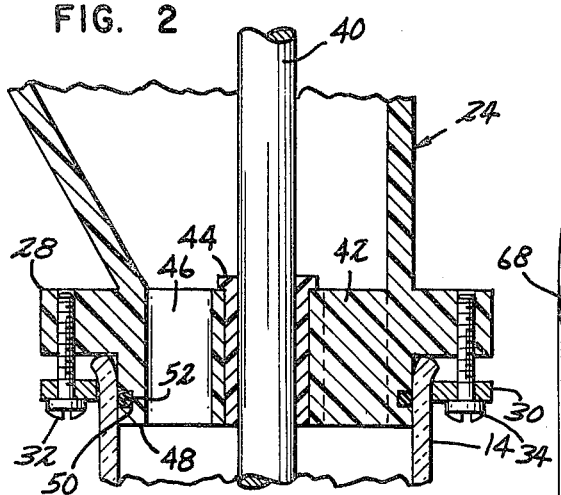
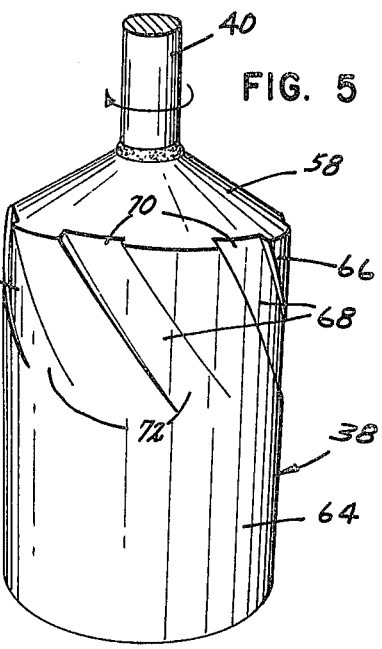
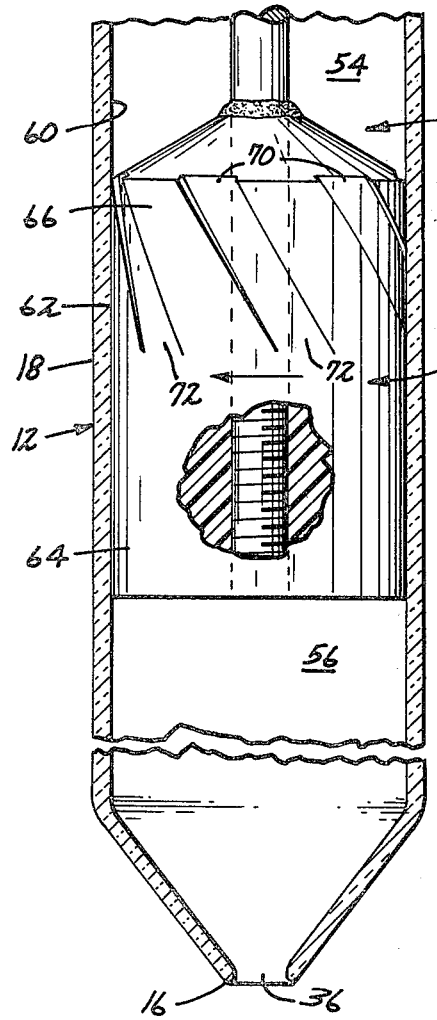
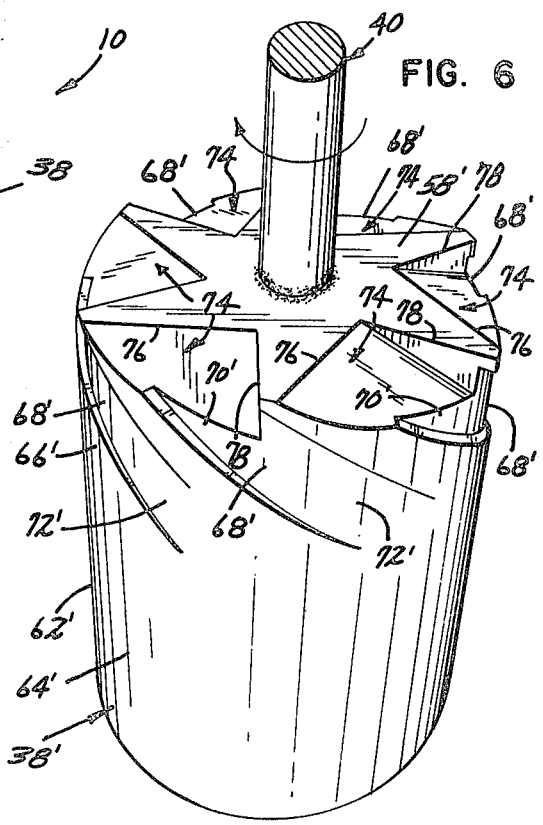

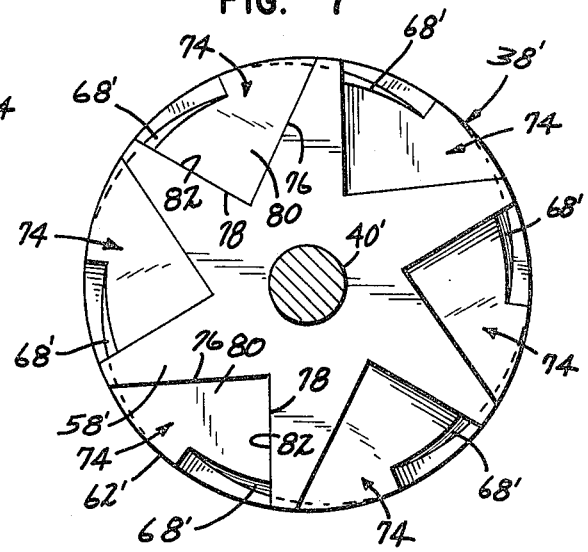
FIG. 7
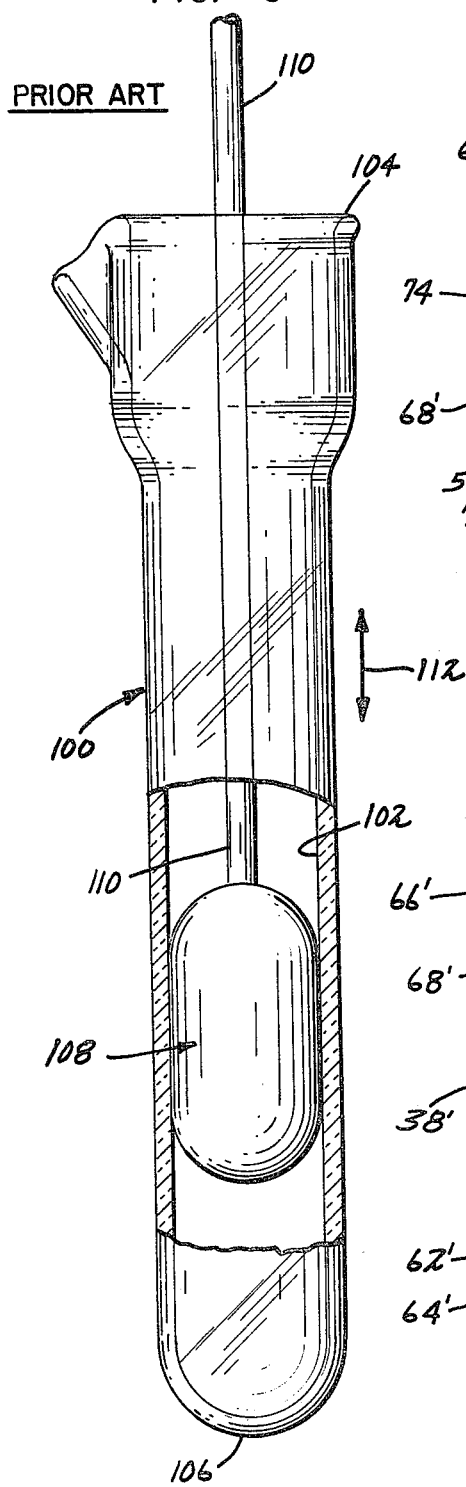
FIG. 9 PRIOR ART
FIG. 8

CONTINUOUS FLOW TISSUE HOMOGENIZER

TECHNICAL FIELD

The present invention relates broadly to the field of subcellular biological research. More specifically, the present invention relates to an apparatus for cell disruption of animal tissue to isolate subcellular organelles. The present invention is especially suited for the isolation of nuclei from animal organs and tissues.

Biologists in great numbers are turning to subcellular research in their efforts to combat disease and learn more about the roles subcellular matter plays in the life processes. As part of this research, it becomes necessary to isolate the subcellular organelles. Isolation includes disruption or breaking apart the cell membranes without damaging the organelles, such as the cell nuclei. Subcellular research programs typically require significant volumes of tissue that must be homogenized such that the appropriate organelles can be isolated therefrom. The apparatus of the present invention provides homogenized tissue in the appropriate quantities while at the same time maintaining high yield of isolated organelles.

PRIOR ART

The prior art tissue homogenization systems include apparatus that is essentially a closed system of limited capacity. The prior art apparatus includes a container with a precision ground inner surface into which limited quantities of the tissue in liquid suspension may be placed. A pestle is designed to be received within the container with a preselected clearance between the surface of the pestle and the side wall of the container. The container or pestle may then be manually reciprocated along the axis of the pestle whereby the tissue is broken apart by the shearing action of the pestle in conjunction with the inner side wall of the container. Once the homogenization is complete the pestle is removed from the container and the homogenized solution may be poured therefrom. The container can then be refilled with additional tissue to be homogenized.

It can be readily understood that the prior art apparatus was extremely time consuming. The apparatus required constant attention and manipulation by a technician. Further, the prior art apparatus is somewhat hazardous in that the technician in operating the device typically is required to grasp the container which is conventionally precision ground glass. It is not uncommon for the glass to shatter, endangering the operating technician.

It is desirable to have a large capacity tissue homogenizer that requires a minimum of operator attention and handling thereby reducing the time required to produce large quantities of homogenized tissue with reduced required technician man-hours and exposure to potential risk. The present invention solves these problems associated with the prior art in that it is a large capacity continuous flow tissue homogenizer. The tissue to be homogenized may be introduced in solution into the homogenizer in a continuous manner with the homogenized solution extracted therefrom with minimum technician attention. In laboratory experimentation it has been determined that the present invention significantly increases the output quantity of homogenized tissue while at the same time maintaining high quality yield of the desired organelles. By requiring minimum manual operations, potential hazard to the laboratory technician is significantly reduced.

SUMMARY OF THE INVENTION

The present invention is a continuous flow tissue homogenizer that includes a housing with first and second ends and a continuous side wall therebetween defining a tissue homogenization chamber. The first end has an inlet and the second end has an outlet for the introduction of the non-homogenized tissue and discharge of homogenized tissue, respectively. A first means disposed within the homogenizing chamber has a working surface cooperating with the inner side wall of the chamber for tissue reduction therebetween. The first means has an axis of rotation aligned generally between the first and second ends of the housing. A second means is provided to rotatably drive said first means about the rotational axis.

In the preferred embodiment, the first means is a pestle member dividing the homogenization chamber into first and second chamber portions. The pestle member has a generally cylindrical outer surface that is spaced apart from the inner side wall to provide fluid communication between the first and second chamber portions and to define a tissue reduction zone between said side wall and said outer surface. The pestle member further has a plurality of spaced grooves in its outer surface at the end of the pestle member proximate the first chamber portion.

The grooves are circumferentially spaced about the pestle member and have a leading portion that opens into the first chamber and a trailing portion. The grooves have a depth that gradually decreases from the leading to the trailing portions.

The pestle member includes a tissue feed portion in which the circumferentially spaced grooves are placed and a tissue reduction portion proximate the second chamber portion. In operation, tissue to be homogenized is introduced in a solution through the inlet into the first chamber portion of the homogenizer. The tissue solution is channeled by the grooves between the outer surface of the pestle member and side wall of the chamber to the tissue reduction portion of the pestle member. The outer surface of the pestle member is spaced apart from the inner side wall such that upon rotation of the pestle member a gentle shearing of the tissue occurs, specifically at the tissue reduction portion of the pestle member. The homogenized tissue solution empties into the second chamber portion from which it is discharged through In an alternative embodiment, the pestle member has a top surface in which a plurality of cut-out portions are provided to define recesses into which the tissue solution is collected. Each of the recesses is in fluid communication with one of the grooves. The recesses are particularly advantageous in the collection of larger pieces of tissue and the channeling of the larger pieces into the grooves and thus to the tissue reduction zone of the apparatus.

The means for rotatably driving the pestle member is typically a conventional motor operatively connected to the pestle member by a shaft or rod extending from the housing. It will become apparent that in the present invention, homogenate can be continuously generated in large quantities utilizing the present invention. Further, it can be seen that the tissue homogenizer of the present invention requires minimum laboratory technician attention and handling, significantly reducing the man-hours expended and the hazard associated with the prior art manual apparatus. The present invention is thus particularly suited to large scale subcellular research of the type that is now being conducted. These and other advantages of the present invention will become more apparent with reference to the accompanying drawings, detailed description of the preferred embodiment, and the claims.

BRIEF DESCRIPTION OF THE DRAWINGS

FIG. 1 is a view in perspective illustrating the continuous flow homogenizer of the present invention;

FIG. 2 is an enlarged partial sectional view in elevation of the apparatus shown in FIG. 1;

FIG. 3 is an enlarged plan view in section taken generally along the lines 3-3 of FIG. 1;

FIG. 4 is an enlarged plan view in section taken generally along lines 4-4 of FIG. 1;

FIG. 5 is a view in perspective illustrating the pestle member of one embodiment of the present invention;

FIG. 6 is a view in perspective illustrating an alternative embodiment of the pestle member of the present invention;

FIG. 7 is a plan view of the alternative embodiment of the pestle member as shown in FIG. 6;

FIG. 8 is a view in elevation of the alternative embodiment of the pestle member as shown in FIG. 6;

FIG. 9 is a view in elevation with parts thereof broken away of the prior art tissue homogenizer.

DETAILED DESCRIPTION OF THE INVENTION

Referring to the drawings, wherein like numerals represent like parts throughout the several views, FIG. 1 is a view in perspective showing the tissue homogenizer of the present invention designated generally at 10. Homogenizer 10 includes a container 12 having a first or inlet end at 14 and a second or outlet end at 16. In the preferred embodiment, container 12 is tubular with a continuous side wall 18 extending between ends 14 and 16 defining a tissue homogenization chamber 19. Container 12 is shown as mounted in members 20 and 22 in a generally vertical orientation. It should be understood that mounting members 20 and 22 are merely illustrative and that any convenient means for mounting container 12 may be utilized.

Disposed at inlet end 14 of container 12 is a receptacle member 24. Receptacle member 24 is shown as generally frusto-conical in shape, but it should be understood that member 24 can be of any convenient cross-sectional configuration. Receptable member 24 is open at its end 26 to receive quantity of tissue in solution. The opposite end of member 24 is provided with a flange portion 28 that is secured to a flange member 30 that extends about end 14 of container 12. The flange member 30 is secured to flange portion 28 by any convenient fastening means as shown at 32 and 34.

Outlet end 16 of container 12 is provided with an outlet opening at 36. A pestle member 38 is sized to be received within container 12. Pestle member 38 is generally cylindrical in shape and is secured to a shaft 40. Shaft 40 has a rotational axis that is aligned with the central axis of pestle member 38. Receptacle member 24 has a plurality of shaft support members 42 that project radially inward and are disposed proximate flange portion 28. Support members 42 define a bearing member 44 in which is received shaft 40. Member 44 may be any convenient bearing means for rotatably receiving shaft 40. Support members 42 define openings 46 at the bottom end 48 of receptacle member 24. Openings 46 provide fluid communication between receptacle member 24 and container 12. A recess 50 may be provided in the outer surface of receptacle member 24 at bottom end 48 and a sealing O-ring 52 may be received within recess 50. Shaft 40 extends through end 26 of receptable member 24 and may be attached to any conventional motor means (not shown) whereby shaft 40 and pestle 38 may be rotatably driven.

With reference specifically to FIGS. 2-5, one embodiment of pestle 38 is disclosed. Pestle 38 is received within container 12 and serves to divide the container into a first chamber 54 and a second chamber 56. As stated previously, pestle member 38 is substantially cylindrical in shape and in the embodiment illustrated has a top portion 58 that is substantially frusto-conical. Side wall 18 of container 12 has a precision ground inner surface 60. The diameter of pestle member 38 is selected such that the clearance between inner surface 60 and an outer surface 62 of pestle member 38 is in the range of 0.0005-0.002 inches for isolation of cell nuclei and other organelles. In general, the clearance between surfaces 60 and 62 is selected in accordance with the size of the organelles to be isolated. A clearance as great as 0.005 could be utilized if whole cell isolation were desired.

Pestle member 38 can be described as having a tissue disruption portion 64 and a tissue feed portion 66. A plurality of grooves or recesses 68 are provided in tissue feed portion 66. In the preferred embodiment, grooves 68 are circumferentially spaced about pestle member 38 and can be described as having a leading portion 70 disposed proximate the base of top portion 58 and a trailing portion 72 terminating at tissue disruption portion 64. Typically, grooves 68 may have a depth on the order of ⅛ inch at leading portion 70. The depth of grooves 70 decreases gradually from a maximum at leading edge portion 70 to a minimum at trailing portion 72. In particular, at trailing portion 72 groove 68 tapers to the maximum outside diameter of pestle member 38. The definitions of leading and trailing with respect to the grooves 68 can be referenced to the direction of rotation of pestle member 38 as shown specifically in FIG. 5.

The operation of the present invention incorporating the embodiment of pestle member 38 shown specifically in FIGS. 1-5 will now be described. Tissue that is to be homogenized is placed in solution and subjected to bulk or gross large particle homogenization in a conventional blade homogenizer, such as a prior art blender. The tissue thus homogenized preferably to pieces less than one centimeter in diameter is introduced into container member 24. The tissue solution passes through openings 46 and fills first chamber 54. The motor means driving pestle member 38 is turned on and pestle member 38 is rotated at a speed typically between 200-1000 revolutions per minute. The direction of rotation as shown in the drawings can be defined as clockwise. The tissue solution within first chamber 54 is collected in grooves 68 which channel the tissue solution to tissue disruption portion 64. The close clearance between inner surface 60 and outer surface 62 results in a gentle shearing action thereby breaking apart cells captured between surface 62 at tissue disruption portion 64 and inner surface 60 of container 12. The homogenized solution empties into second chamber 56 and is discharged from container 12 through opening 36. The homogenized solution is then collected and the organelles are separated therefrom through other methods that do not form a part of the present invention.

From the above description, it is apparent that the present invention is a continuous flow tissue homogenizer. The tissue solution may be continuously introduced above pestle member 38, subjected to gentle tissue disruption, and the homogenate discharged through opening 36. In the preferred embodiment, container 12 is a precision bore glass receptacle and pestle member 38 is formed of Teflon. Through usage, inner surface 60 may become worn and therefore the clearance between inner surface 60 and outer surface 62 may become unacceptable over extended operation. In this event, the pestle member 38 may simply be disposed at an alternate position along the central axis of container 12, i.e., at a position where side wall 60 has not been subjected to the cooperating shearing action of surfaces 60 and 62. Thus, the useful life of the precision bore container 12 is significantly increased.

FIGS. 6-8 illustrate a second embodiment of the pestle member and is designated generally as 38'. Pestle member 38' is substantially cylindrical in shape and is mounted to shaft 40' along its central axis. Pestle member 38' has an outer surface 62', a tissue disruption portion 64' and a tissue feed portion 66'. Pestle member 38' has a top portion 58' that is substantially planar with a surface lying in a plane perpendicular to the central axis of pestle member 38'. Tissue feed portion 66' is provided with a plurality of grooves or recesses 68'. Grooves 68' have a leading portion 70' proximate the outer edge of top portion 58' and a trailing portion 72' proximate tissue disruption portion 64. Grooves 68' are circumferentially spaced about the central axis of pestle member 38'.

Top portion 58' has a plurality of cut-out portions 74 formed therein. A cut-out portion 74 is provided corresponding to each groove 68'. Each cut-out portion has a leading edge at 76 and a trailing edge at 78. The depth of the cut-out portions 74 gradually increase from the leading edge 76 toward the trailing edge 78. Each cut-out portion is defined by a leading to trailing edge wall member 80 and a wall member 82 that essentially lies in the radial plane with respect to the central axis of pestle member 38'. Cut-out portions 74 open into grooves 68' at leading portions 70' thereof. Cut-out portions 74 function to collect larger tissue particles as pestle member 38' rotates in a clockwise direction as illustrated in the drawings. The collected larger size tissue particles are thereby channeled into grooves 68' where they are then fed toward tissue disruption portion 64' of pestle member 38'. Grooves 68' are again formed such that the depth of the groove decreases gradually from leading portion 74' to trailing portion 72'.

Pestle member 38' may therefore be used when it is desired to collect larger size tissue particles from the tissue solution that is introduced above pestle member 38' into first chamber 54 than would be possible using pestle member 38. Pestle member 38' has been found to be particularly useful when whole soft tissue is being homogenized (thereby eliminating the step of large particle disruption by blender) and when there are relatively large pieces of soft to medium tough tissue present in the solution. Otherwise, the operation of pestle member 38' is identical to that previously described with reference to pestle member 38.

FIG. 9 illustrates prior art tissue homogenization apparatus typically in use preceding the present invention. The prior art device includes a container 100, typically a glass receptacle, with a precision bore inner side wall 102. Container 100 is open at its top end 104 and closed at its bottom end 106. A pestle member 108 is adapted to be received within container 100 in close tolerance with precision bore side wall 102. The clearance between pestle member 108 and side wall 102 may be selected as described above with reference to the present invention. Pestle member 108 is typically affixed to a rod or shaft member 110. In the prior art homogenization method, rod 110 is typically held in a stationery position. The tissue to be homogenized is poured into container 100. Pestle member 108 is then placed within container 100 and the container is reciprocated axially as shown by the arrows at 112. Container 100 is manually reciprocated by the laboratory technician. When the tissue is homogenized to the desired extent, container 100 is removed from pestle member 108 and the homogenized tissue in solution is poured therefrom. Non-homogenized tissue in solution can then be poured into container 100 and the process repeated.

From the above description, it is clear that the prior art tissue homogenization apparatus has much less capacity than the present invention and consumes significantly more laboratory technician time. The present invention is a continuous flow homogenizer capable of producing homogenate in large quantities with efficient yield of nuclei or other desired organelles. In practice, it has been found that the homogenizer of the present invention generates the same quantity of homogenate as in the prior art on the order of twenty to fifty times faster than with the prior art apparatus. While the present invention has been disclosed with particular reference to isolation of cell nuclei, it should be understood that the present invention has applicability to the isolation of other organelles. Specifically, interchangeable pestle members sized for varying clearances with the container sidewall may be used according to the size of the organelle to be isolated. In the preferred embodiment of the present invention, the container 12 has been disclosed as a precision bore glass tubing and pestle members 38 and 38' are disclosed as made of Teflon. It should be understood however, that alternative material could be utilized within the spirit and scope of the present invention.

What is claimed is:

1. A continuous flow tissue homogenizer for subcellular organelle isolation comprising:
   (a) a tubular housing defining a tissue homogenizing chamber, said housing having first and second ends and a continuous smooth inner side wall therebetween, said first end having an inlet for introduction of non-homogenized tissue and said second end having an outlet continuously open for the discharge of homogenized tissue;
   (b) a cylindrical pestle member disposed within said homogenizing chamber and having a smooth outer surface cooperating with said continuous side wall for tissue disruption therebetween, said cylindrical pestle member rotatable about an axis aligned with the elongation axis of said housing;
   (c) means for rotatably driving said cylindrical pestle member whereby said outer surface and said inner side wall cooperate to gently shear cell membranes to isolate large quantities of organelles; and
   (d) said outer surface of said pestle member and said inner side wall of said tubular housing spaced apart to shear cell membranes without damage to organelles.

2. A continuous flow tissue homogenizer in accordance with claim 1 wherein said outer surface and said inner side wall are spaced apart in a range of 0.0005–0.002 inches.

3. A continuous flow tissue homogenizer in accordance with claim 1 wherein said pestle member divides said homogenizing chamber into an inlet zone and an outlet zone and has a first tissue feed portion proximate said inlet zone and a tissue disruption portion proximate said outlet zone, said tissue feed portion provided with a plurality of grooves in its outer surface circumferentially spaced apart about said rotational axis, each of said grooves having a depth that gradually decreases from an end of said pestle member proximate said inlet zone and terminating at said tissue disruption portion whereby tissue is drawn into the spacing between said outer wall of said pestle member and said inner side wall at said tissue disruption portion.

4. A continuous flow tissue homogenizer for subcellular organelle isolation comprising:
(a) a container member having a generally cylindrical tissue homogenization chamber, said container having an inlet opening at one end thereof, and an outlet continuously open at the opposite end thereof;
(b) a pestle member disposed within said chamber and dividing said chamber into a first chamber into which said inlet opens and a second chamber into which said outlet is continuously open, said pestle member having a rotational axis and an outer surface spaced apart from the inner side wall of said container member to provide fluid communication between said first and second chambers, said pestle member having a first tissue feed portion proximate said first chamber and a tissue disruption portion proximate said second chamber, said tissue feed portion provided with a plurality of grooves circumferentially spaced about the outer surface of said pestle member, each of said grooves opening into and extending from said first chamber to said tissue disruption portion, each of said grooves having a depth that gradually decreases from said first chamber to said tissue disruption portion to draw tissue into a tissue disruption zone defined by the clearance between said tissue disruption portion and said inner side wall; and
(c) means for rotatably driving said pestle member about its rotational axis to gently shear cell membranes and isolate large quantities of organelles.

5. A continuous flow tissue homogenizer in accordance with claim 4 further comprising means for channeling tissue in said first chamber into said grooves.

6. A continuous flow tissue homogenizer in accordance with claim 5 wherein said means for channeling tissue comprises a top surface of said feed portion of said pestle, said top surface having a plurality of cutout portions defining recesses into which tissue is collected, each of said recesses being in fluid communication with one of said grooves.

7. A continuous flow tissue homogenizer for subcellular organelle isolation comprising:
(a) a tubular housing defining a tissue homogenizing chamber, said housing having first and second ends and a continuous smooth inner side wall therebetween, said first end having an inlet for introduction of non-homogenized tissue and said second end having an outlet continuously open for the discharge of homogenized tissue;
(b) a cylindrical pestle member disposed within said housing and adjustably positioned along an elongation axis of said tubular housing, said pestle member having a smooth outer surface cooperating with said continuous side wall for tissue disruption therebetween, said cylindrical pestle member rotatable about an axis aligned with the elongation axis of said housing;
(c) means for rotatably driving said cylindrical pestle member whereby said outer surface and said inner side wall cooperate to gently shear cell membranes to isolate large quantities of organelles; and
(d) said outer surface of said pestle member and said inner side wall of said tubular housing spaced apart to shear cell membranes without damage to organelles.

8. A continuous flow tissue homogenizer in accordance with claim 7 wherein the spacing between said cooperating outer surface and said inner side wall lies in the range of 0.0005–0.002 inches.

9. A continuous flow tissue homogenizer in accordance with claim 7 wherein said pestle member divides said tissue homogenizing chamber into an inlet zone and an outlet zone and has a first tissue feed portion proximate said inlet zone and a tissue disruption portion proximate said outlet zone, said tissue feed portion provided with a plurality of grooves circumferentially spaced about said rotational axis, each of said grooves opening into said inlet zone and terminating at said tissue disruption portion, said grooves also having a depth gradually decreasing from said inlet zone to said tissue disruption portion whereby tissue is drawn into a tissue disruption zone between the outer surface of said tissue disruption portion and said inner side wall.

10. A continuous flow tissue homogenizer in accordance with claim 9 further comprising means for channeling tissue into said grooves, said channeling means comprising a top surface of said feed portion of said pestle member, said top surface having a plurality of cutout portions defining recesses into which tissue is collected, each of said recesses in fluid communication with one of said grooves.

* * * * *